US006461836B1

(12) United States Patent
Elshourbagy et al.

(10) Patent No.: US 6,461,836 B1
(45) Date of Patent: Oct. 8, 2002

(54) MOLECULAR CLONING OF A 7TM RECEPTOR (AXOR34) AND SCREENING METHODS THEREOF

(75) Inventors: Nabil Elshourbagy, West Chester, PA (US); Usman Shabon, Collegeville, PA (US); Robert S. Ames, Havertown, PA (US); Henry S. Sarau, Harleysville, PA (US); Lisa Vawter, Coopersburg, PA (US); David Michalovich, Harlow (GB)

(73) Assignees: SmithKline Beecham Corporation, Philadelphia, PA (US); SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/545,944

(22) Filed: Apr. 10, 2000

Related U.S. Application Data

(63) Continuation-in-part of application No. 09/435,384, filed on Nov. 5, 1999, now abandoned.

(51) Int. Cl.$^7$ .................. C12N 15/12; C12N 15/63; C12N 5/00; C07K 14/00; C07H 21/04
(52) U.S. Cl. ................ 435/69.1; 435/320.1; 435/325; 536/23.5; 530/350
(58) Field of Search ................ 435/69.1, 320.1, 435/325; 536/23.5; 530/350

(56) References Cited

FOREIGN PATENT DOCUMENTS

| EP | 1090990 | 11/2001 |
|----|---------|---------|
| WO | WO 99/55732 | 4/1999 |
| WO | WO 00/31258 | 6/2000 |
| WO | WO 01/25269 | 4/2001 |
| WO | WO 01/48189 | 7/2001 |
| WO | WO 01/57524 | 8/2001 |

OTHER PUBLICATIONS

GenBank Accession No. R37725, L. Hillier, et al., "The WashU–Merck EST Project", (May 4, 1995).
GenBank Accession No. H11333, L. Hillier, et al., "The WashU–Merck EST Project", (Jun. 26, 1995).
GenBank Accession No. N45474, L. Hillier, et al., "The WashU–Merck EST Project", (Feb. 13, 1996).
GenBank Accession No. R40869, L. Hillier, et al., "The WashU–Merck EST Project", (May 22, 1995).
GenBank Accession No. U60179, A. D. Howard, et al., "A Receptor in Pituitary and Hypothalamus that Functions in Growth Hormone Release", (Aug. 23, 1996).
GenBank Accession No. AI432384, No author listed, instead cities (NCI–CGAP http://www.ncbi.nlm.nih.gov/ncicgap) "National Cancer Institute, Cancer Genome Anatomy Project (CGAP) Tumor Gene Index", (Mar. 30, 1999).
GenBank Accession No. W61169, L. Hillier, et al., "The WashU–Merck EST Project", (Oct. 15, 1996).
GenBank Accession No. F03770, C. Auffray, et al., "Image: Molecular Integration of the Human Genome and its Expressioin" (Feb. 19, 1995).
GenBank Accession No. F01358, C. Auffray, et al., "Image: Molecular Integration of the Analysis of the Human Genome and its Expression" (Feb. 1, 1995).
GenBank Acession No. AI023570, No author listed, instead cities (NCI–CGAP http://www.ncbi.nlm.nih.gov/ncicgap) "National Cancer Institute, Cancer Genome Anatomy Project (CGAP) Tumor Gene Index", (Jun. 18, 1998).
GenBank Accession No. Z38158, C. Auffray, et al., "Image: Molecular Integration of the Analysis of the Human Genome and its Expression", (Oct. 27, 1994).
Howard, et al., "A Receptor in Pituitary and Hypothalamus that Functions in Growth Hormone Release", *Science*, 273: 974–977 (1996).

*Primary Examiner*—David S. Romeo
*Assistant Examiner*—Joseph F. Murphy
(74) *Attorney, Agent, or Firm*—Elizabeth J. Hecht; Edward R. Gimmi; Charlie M. Kinzig

(57) ABSTRACT

AXOR34 polypeptides and polynucleotides and methods for producing such polypeptides by recombinant techniques are disclosed. Also disclosed are methods for utilizing AXOR34 polypeptides and polynucleotides in diagnostic assays. Further disclosed are screening assays to identify agonists and antagonists of the interaction between AXOR34 and its ligands, NmU-8, NmU-25, and NmU-23.

8 Claims, 5 Drawing Sheets

Figure 1

SEQ ID NO:1
```
ATGTCAGGGATGGAAAAACTTCAGAATGCTTCCTGGATCTACCAGCAGAAACTAGAAGAT
CCATTCCAGAAACACCTGAACAGCACCGAGGAGTATCTGGCCTTCCTCTGCGGACCTCGG
CGCAGCCACTTCTTCCTCCCCGTGTCTGTGGTGTATGTGCCAATTTTTGTGGTGGGGGTC
ATTGGCAATGTCCTGGTGTGCCTGGTGATTCTGCAGCACCAGGCTATGAAGACGCCCACC
AACTACTACCTCTTCAGCCTGGCGGTCTCTGACCTCCTGGTCCTGCTCCTTGGAATGCCC
CTGGAGGTCTATGAGATGTGGCGCAACTACCCTTTCTTGTTCGGGCCCGTGGGCTGCTAC
TTCAAGACGGCCCTCTTTGAGACCGTGTGCTTCGCCTCCATCCTCAGCATCACCACCGTC
AGCGTGGAGCGCTACGTGGCCATCCTACACCCGTTCCGCGCCAAACTGCAGAGCACCCGG
CGCCGGGCCCTCAGGATCCTCGGCATCGTCTGGGGCTTCTCCGTGCTCTTCTCCCTGCCC
AACACCAGCATCCATGGCATCAAGTTCCACTACTTCCCCAATGGGTCCCTGGTCCCAGGT
TCGGCCACCTGTACGGTCATCAAGCCCATGTGGATCTACAATTTCATCATCCAGGTCACC
TCCTTCCTATTCTACCTCCTCCCCATGACTGTCATCAGTGTCCTCTACTACCTCATGGCA
CTCAGACTAAAGAAAGACAAATCTCTTGAGGCAGATGAAGGGAATGCAAATATTCAAAGA
CCCTGCAGAAAATCAGTCAACAAGATGCTGTTTGTCTTGGTCTTAGTGTTTGCTATCTGT
TGGGCCCCGTTCCACATTGACCGACTCTTCTTCAGCTTTGTGGAGGAGTGGACTGAATCC
CTGGCTGCTGTGTTCAACCTCGTCCATGTGGTGTCAGGTGTCTTATTCTACCTGAGCTCA
GCTGTCAACCCCATTATCTATAACCTACTGTCTCGCCGCTTCCAGGCAGCATTCCAGAAT
GTGATCTCTTCTTTCCACAAACAGTGGCACTCCCAGCATGACCCACAGTTGCCACCTGCC
CAGCGGAACATCTTCCTGACAGAATGCCACTTTGTGGAGCTGACCGAAGATATAGGTCCC
CAATTCCTATGTCAGTCATCCGTGCACAACTCTCACCTCCCAACAGCCCTCTCTAGTGAA
CAGATGTCAAGAACAAACTATCAAAGCTTCCACTTTAACAAAACCTGA
```

Figure 2

SEQ ID NO:2

```
  1  MSGMEKLQNA  SWIYQQKLED  PFQKHLNSTE  EYLAFLCGPR  RSHFFLPVSV
 51  VYVPIFVVGV  IGNVLVCLVI  LQHQAMKTPT  NYYLFSLAVS  DLLVLLLGMP
101  LEVYEMWRNY  PFLFGPVGCY  FKTALFETVC  FASILSITTV  SVERYVAILH
151  PFRAKLQSTR  RRALRILGIV  WGFSVLFSLP  NTSIHGIKFH  YFPNGSLVPG
201  SATCTVIKPM  WIYNFIIQVT  SFLFYLLPMT  VISVLYYLMA  LRLKKDKSLE
251  ADEGNANIQR  PCRKSVNKML  FVLVLVFAIC  WAPFHIDRLF  FSFVEEWTES
301  LAAVFNLVHV  VSGVLFYLSS  AVNPIIYNLL  SRRFQAAFQN  VISSFHKQWH
351  SQHDPQLPPA  QRNIFLTECH  FVELTEDIGP  QFLCQSSVHN  SHLPTALSSE
401  QMSRTNYQSF  HFNKT
```

Figure 3

SEQ ID NO:3

1    YFLFRPRN

Figure 4

SEQ ID NO:4

```
1    FLVDEEFQGP IVSQNRRYFL FRPRN
```

Figure 5

SEQ ID NO:5

```
1    YKVNEYQGPV APSGGFFLFR PRN
```

MOLECULAR CLONING OF A 7TM RECEPTOR (AXOR34) AND SCREENING METHODS THEREOF

CROSS-REFERENCE TO RELATED APPLICATIONS

This application is a continuation-in-part application of U.S. application Ser. No. 09/435,384, filed Nov. 5, 1999, now abandoned, the entire disclosure of which is herein incorporated by reference.

FIELD OF THE INVENTION

This invention relates to newly identified polypeptides and polynucleotides encoding such polypeptides, to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics," that is, high throughput genome- or gene-based biology. This approach as a means to identify genes and gene products as therapeutic targets is rapidly superseding earlier approaches based on "positional cloning." A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterize further genes and their related polypeptides/proteins, as targets for drug discovery.

It is well established that many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide, GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histarnine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said sockets being surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson, et al., Endoc. Rev., 1989, 10:317–331). Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7 TM) receptors have been successfully introduced onto the market.

SUMMARY OF THE INVENTION

In one aspect, the present invention relates to AXOR34, in particular AXOR34 polypeptides and AXOR34 polynucleotides, recombinant materials and methods for their production. Such polypeptides and polynucleotides are of interest in relation to methods of treatment of certain diseases, including, but not limited to, infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergies; benign prostatic hypertrophy; migraine; vomiting; psychotic and neurological disorders, including anxiety, schizophrenia, manic depression, depression, delirium, dementia, and severe mental retardation; and dyskinesias, such as Huntington's disease or Gilles dela Tourett's syndrome, hereinafter referred to as "diseases of the invention". In a further aspect, the invention relates to methods for identifying agonists and antagonists (e.g., inhibitors) using the materials provided by the invention, and treating conditions associated with AXOR34 imbalance with the identified compounds. In a still further aspect, the invention relates to diagnostic assays for detecting diseases associated with inappropriate AXOR34 activity or levels.

In another aspect, the present invention provides methods of screening for compounds which bind to and activate (agonist) or inhibit activation (antagonist) of human AXOR34 polypeptides (receptors), and for their ligands, porcine Neuromedin U-8 (herein "NmU-8") (SEQ ID NO:3), porcine Neuromedin U-25 (herein "NmU-25") (SEQ ID NO:4), and rat Neuromedin U-23 (herein "NmU-23") (SEQ ID NO:5).

In particular, the preferred method for identifying agonist or antagonist of a human AXOR34 polypeptide comprises:
(a) contacting a cell expressing on the surface thereof the receptor, said receptor being associated with a second component capable of providing a detectable signal in response to the binding of a compound to said receptor, with a compound to be screened under conditions to permit binding to the polypeptide; and
(b) determining whether the compound binds to and activates or inhibits the receptor by measuring the level of a signal generated from the interaction of the compound with the receptor.

In a further preferred embodiment, the method further comprises conducting the identification of an agonist or antagonist in the presence of a labeled or unlabeled Neuromedin U (herein "NmU") selected from the group consisting of: porcine NmU-8 (SEQ ID NO:3), porcine NmU-25 (SEQ ID No:4), and rat NmU-23 (SEQ ID NO:5).

In another embodiment, the method for identifying an agonist or antagonist of a human AXOR34 receptor comprises:
determining the inhibition of binding of a ligand to cells which have the receptor on the surface thereof, or to cell membranes containing the receptor, in the presence of a candidate compound under conditions to permit binding to the receptor, and determining the amount of ligand bound to the receptor, such that a compound capable of causing reduction of binding of a ligand is an agonist or antagonist. Preferably, the ligand is a NmU selected from the group consisting of: porcine NmU-8 (SEQ ID NO:3), porcine NmU-25 (SEQ ID NO:4), and rat NmU-23 (SEQ ID NO:5). Yet more preferably, the NmU (e.g., porcine NmU-8, porcine NmU-25, and rat NmU-23) is labeled.

BRIEF DESCRIPTION OF THE DRAWINGS

FIG. 1 shows the nucleotide sequence of the human AXOR34 receptor (SEQ ID NO:1).

FIG. 2 shows the deduced amino acid sequence of the human AXOR34 receptor (SEQ ID NO:2).

Figure 3:
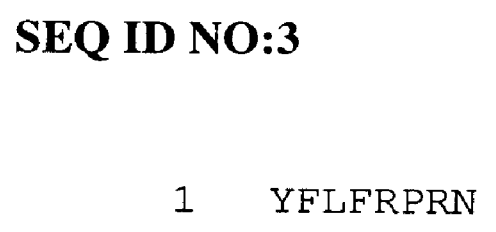

FIG. 3 shows the deduced amino acid sequence of porcine NmU-8 (SEQ ID NO:3).

FIG. 4 shows the deduced amino acid sequence of porcine NmU-25 (SEQ ID NO:4).

Figure 5:
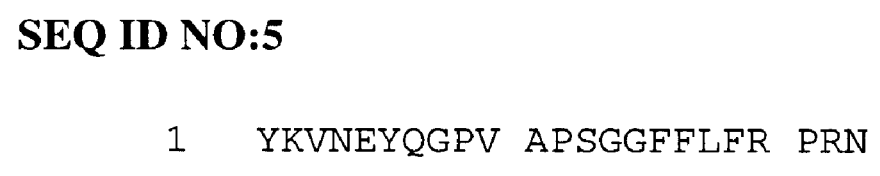

FIG. 5 shows the deduced amino acid sequence of rat NmU-23 (SEQ ID NO:5).

DESCRIPTION OF THE INVENTION

In a first aspect, the present invention relates to AXOR34 polypeptides. Such polypeptides include:
(a) an isolated polypeptide encoded by a polynucleotide comprising the sequence of SEQ ID NO:1;
(b) an isolated polypeptide comprising a polypeptide sequence having at least 95%, 96%, 97%, 98%, or 99% identity to the polypeptide sequence of SEQ ID NO:2;
(c) an isolated polypeptide comprising the polypeptide sequence of SEQ ID NO:2;
(d) an isolated polypeptide having at least 95%, 96%, 97%, 98%, or 99% identity to the polypeptide sequence of SEQ ID NO:2;
(e) the polypeptide sequence of SEQ ID NO:2;
(f) an isolated polypeptide having or comprising a polypeptide sequence that has an Identity Index of 0.95, 0.96, 0.97, 0.98, or 0.99 compared to the polypeptide sequence of SEQ ID NO:2; and
(g) fragments and variants of such polypeptides in (a) to (f).

Polypeptides of the present invention are believed to be members of the G-Protein Coupled 7TMR receptor family of polypeptides. They are therefore of interest because G-protein coupled receptors, more than any other gene family, are targets of pharmaceutical intervention.

The biological properties of AXOR34 are hereinafter referred to as "biological activity of AXOR34" or "AXOR34 activity". Preferably, a polypeptide of the present invention exhibits at least one biological activity of human AXOR34.

Polypeptides of the present invention also include variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO: 2, or an isolated polypeptide comprising an amino acid sequence having at least 30, 50 or 100 contiguous amino acids truncated or deleted from the amino acid sequence of SEQ ID NO: 2. Preferred fragments are biologically active fragments that mediate the biological activity of AXOR34, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, prosequences, sequences that aid in purification, for instance multiple histidine residues, or an additional sequence for stability during recombinant production.

Polypeptides of the present invention can be prepared in any suitable manner, for instance by isolation form naturally occurring sources, from genetically engineered host cells comprising expression systems (vide infra) or by chemical synthesis, using for instance automated peptide synthesizers, or a combination of such methods. Means for preparing such polypeptides are well understood in the art.

In a further aspect, the present invention relates to AXOR34 polynucleotides. Such polynucleotides include:

(a) an isolated polynucleotide comprising a polynucleotide sequence having at least 95%, 96%, 97%, 98%, or 99% identity to the polynucleotide sequence of SEQ ID NO:1;

(b) an isolated polynucleotide comprising the polynucleotide of SEQ ID NO:1;

(c) an isolated polynucleotide having at least 95%, 96%, 97%, 98%, or 99% identity to the polynucleotide of SEQ ID NO:1;

(d) the isolated polynucleotide of SEQ ID NO:1;

(e) an isolated polynucleotide comprising a polynucleotide sequence encoding a polypeptide sequence having at least 95%, 96%, 97%, 98%, or 99% identity to the polypeptide sequence of SEQ ID NO:2;

(f) an isolated polynucleotide comprising a polynucleotide sequence encoding the polypeptide of SEQ ID NO:2;

(g) an isolated polynucleotide having a polynucleotide sequence encoding a polypeptide sequence having at least 95%, 96%, 97%, 98%, or 99% identity to the polypeptide sequence of SEQ ID NO:2;

(h) an isolated polynucleotide encoding the polypeptide of SEQ ID NO:2;

(i) an isolated polynucleotide having or comprising a polynucleotide sequence that has an Identity Index of 0.95, 0.96, 0.97, 0.98, or 0.99 compared to the polynucleotide sequence of SEQ ID NO:1;

j) an isolated polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and polynucleotides that are fragments and variants of the above mentioned polynucleotides or that are complementary to above mentioned polynucleotides, over the entire length thereof.

Preferred fragments of polynucleotides of the present invention include an isolated polynucleotide comprising an nucleotide sequence having at least 15, 30, 50 or 100 contiguous nucleotides from the sequence of SEQ ID NO: 1, or an isolated polynucleotide comprising an sequence having at least 30, 50 or 100 contiguous nucleotides truncated or deleted from the sequence of SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptide of SEQ ID NO:2;

(b) is the RNA transcript of the DNA sequence encoding the polypeptide of SEQ ID NO:2;

(c) comprises an RNA transcript of the DNA sequence of SEQ ID NO:1; or (d) is the RNA transcript of the DNA sequence of SEQ ID NO:1; and RNA polynucleotides that are complementary thereto.

The polynucleotide sequence of SEQ ID NO:1 shows homology with Human Growth Hormone Secretagogue receptor type 1 [A. D. Howard, et. al., Science 273 (5277), 974–977. (1996)]. The polynucleotide sequence of SEQ ID NO:1 is a cDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO:1, which, as a result of the redundancy (degeneracy) of the genetic code, also encodes the polypeptide of SEQ ID NO:2. The polypeptide of SEQ ID NO:2 is related to other proteins of the G-Protein Coupled 7TMR family, having homology and/or structural similarity with Human Growth Hormone Secretagogue receptor type 1 [A. D. Howard, et. al. Science, 273 (5277), 974–977 (1996)].

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one AXOR34 activity.

Polynucleotides of the present invention may be obtained using standard cloning and screening techniques from a cDNA library derived from mRNA in cells of human brain and testis, (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro- protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerization reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adapter specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al.(ibid). Preferred methods of introducing polynucleotides into host cells include, for instance, calcium phosphate transfection, DEAE-dextran mediated transfection, transvection, micro-injection, cationic lipid-mediated transfection, electroporation, transduction, scrape loading, ballistic introduction or infection.

Representative examples of appropriate hosts include bacterial cells, such as Streptococci, Staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of wellknown and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterized by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled AXOR34 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and SI protection or the chemical cleavage method (see Cotton et al., Proc Natl Acad Sci USA (1985) 85: 4397–4401).

An array of oligonucleotides probes comprising AXOR34 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610≧613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radio-immunoassays, competitive-binding assays, Western Blot analysis and ELISA assays.

Thus in another aspect, the present invention relates to a diagnostic kit comprising:
  (a) a polynucleotide of the present invention, preferably the nucleotide sequence of SEQ ID NO: 1, or a fragment or an RNA transcript thereof;
  (b) a nucleotide sequence complementary to that of (a);
  (c) a polypeptide of the present invention, preferably the polypeptide of SEQ ID NO:2 or a fragment thereof; or
  (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localization studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet 1996 Mar;5 (3):339–46 A radiation hybrid map of the human genome. Gyapay G, Schmitt K, Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 5q32.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hybridization techniques to clones arrayed on a grid, such as cDNA microarray hybridization (Schena et al, Science, 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in the brain and testis.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Imunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intra-muscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

The human AXOR34 polypeptide (receptor of the present invention) may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan, et al., *Current Protocols in Immunology* 1(2):Chapter 5 (1991).

AXOR34 proteins are ubiquitous in the mammalian host and are responsible for many biological functions, including many pathologies. Accordingly, it is desirous to find compounds and drugs which stimulate AXOR34, on the one hand, and which can inhibit the function of AXOR34, on the other hand. In general, agonists are employed for therapeutic and prophylactic purposes for such conditions as infections such as infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergies; benign prostatic hypertrophy; migraine; vomiting; psychotic and neurological disorders, including anxiety, schizophrenia, manic depression, depression, delirium, dementia, and severe mental retardation; and dyskinesias, such as Huntington's disease or Gilles dela Tourett's syndrome, among others.

In general, such screening procedures involve providing appropriate cells which express a receptor polypeptide of the present invention on the surface thereof. Such cells include cells from mammals, yeast, Drosophila or *E. coli*. In particular, a polynucleotide encoding the receptor of the present invention is employed to transfect cells to thereby express a human AXOR34 polypeptide. The expressed receptor is then contacted with a test compound to observe binding, stimulation or inhibition of a functional response.

One such screening procedure involves the use of melanophores which are transfected to express the human AXOR34 polypeptide. Such a screening technique is described in PCT WO 92/01810, published Feb. 6, 1992. Such an assay may be employed to screen for a compound which inhibits activation of a receptor of the present invention by contacting the melanophore cells which encode the receptor with both a receptor ligand, such as porcine NmU-8 (SEQ ID NO:3), porcine NmU-25 (SEQ ID NO:4), and rat NmU-23 (SEQ ID NO:5), and a compound to be screened. Inhibition of the signal generated by the ligand indicates that a compound is a potential antagonist for the receptor, i.e., inhibits activation of the receptor.

The technique may also be employed for screening of compounds which activate a receptor of the present invention by contacting such cells with compounds to be screened and determining whether such compound generates a signal, i.e., activates the receptor.

Other screening techniques include the use of cells which express the human AXOR34 polypeptide (for example, transfected CHO cells) in a system which measures extracellular pH changes caused by receptor activation. In this technique, compounds may be contacted with cells expressing a receptor polypeptide of the present invention. A second messenger response, e.g., signal transduction or pH changes, is then measured to determine whether the potential compound activates or inhibits the receptor.

Another screening technique involves expressing a human AXOR34 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists, and thus inhibit activation of a receptor polypeptide of the present invention by determining inhibition of binding of a labeled ligand, such NmU (e.g., porcine NmU-8 (SEQ ID NO:3), porcine NmU-25 (SEQ ID NO:4), and rat NmU-23 (SEQ ID NO:5), to cells which have the receptor on the surface thereof, or cell membranes containing the receptor. Such a method involves transfecting a eukaryotic cell with a DNA encoding a human AXOR34 polypeptide such that the cell expresses the receptor on its surface. The cell is then contacted with a potential antagonist in the presence of a labeled form of a ligand, such as NmU (e.g., porcine NmU-8 (SEQ ID NO:3), porcine NmU-25 (SEQ ID NO:4), and rat NmU-23 (SEQ ID NO:5)). The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another such screening procedure involves the use of mammalian cells which are transfected to express a receptor of the present invention. The cells are loaded with an indicator dye that produces a fluorescent signal when bound to calcium, and the cells are contacted with a test substance and a receptor agonist, such as NmU (e.g., porcine NmU-8 (SEQ ID NO:3), porcine NmU-25 (SEQ ID NO:4), and rat NmU-23 (SEQ ID NO:5)). Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist (or agonist) for the receptor.

Another such screening procedure involves use of mammalian cells which are transfected to express a receptor of the present invention, and which are also transfected with a reporter gene construct that is coupled to activation of the receptor (for example, luciferase or β-galactosidase behind an appropriate promoter). The cells are contacted with a test substance and a receptor agonist, such as NmU (e.g., porcine NmU-8 (SEQ ID NO:3), porcine NmU-25 (SEQ ID NO:4), and rat NmU-23 (SEQ ID NO:5)), and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another such screening technique for antagonists or agonists involves introducing RNA encoding the human AXOR34 polypeptide into Xenopus oocytes to transiently or stably express the receptor. The receptor oocytes are then contacted with a receptor ligand, such as NmU (e.g., porcine NmU-8 (SEQ ID NO:3), porcine NmU-25 (SEQ ID NO:4), and rat NmU-23 (SEQ ID NO:5)), and a compound to be screened. Inhibition or activation of the receptor is then determined by detection of a signal, such as, cAMP, calcium, proton, or other ions.

Another method involves screening for human AXOR34 polypeptide inhibitors by determining inhibition or stimulation of human AXOR34 polypeptide-mediated cAMP and/ or adenylate cyclase accumulation or dimunition. Such a method involves transiently or stably transfecting a eukaryotic cell with a human AXOR34 polypeptide to express the receptor on the cell surface. The cell is then exposed to potential antagonists in the presence of AXOR34 polypeptide ligand, such as NmU (e.g., porcine NmU-8 (SEQ ID NO:3), porcine NmU-25 (SEQ ID NO:4), and rat NmU-23 (SEQ ID NO:5)). The amount of cAMP accumulation is then measured, for example, by radio-immuno or protein binding assays (e.g., using Flashplates or a scintillation proximity assay). Changes in cAMP levels can also be determined by directly measuring the activity of the enzyme, adenylyl cyclase, in broken cell preparations. If the potential antagonist binds the receptor, and thus inhibits human AXOR34 polypeptide binding, the levels of human AXOR34 polypeptide-mediated cAMP, or adenylate cyclase activity, will be reduced or increased.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATα. Each cell type secretes a small peptide hormone that binds to a G-protein coupled receptor on opposite mating-type cells which triggers a MAP kinase cascade leading to G1 arrest as a prelude to cell fusion. Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometric readout, depending on the specific reporter construct used (e.g., β-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J. *Nature* 384: 14–16, 1996; Manfredi, et al., *Mol. Cell. Biol.* 16: 4700–4709, 1996). This provides a rapid direct growth selection (e.g., using the FUS1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands. Functional agonists of sufficient potency (whether natural or surrogate) can be used as screening tools in yeast cell-based assays for identifying G-protein coupled receptor antagonists. For this purpose, the yeast system offers advantages over mammalian expression systems due to its ease of utility and null receptor background (lack of endogenous G-protein coupled receptors) which often interferes with the ability to identify agonists or antagonists.

The present invention also provides a method for determining whether a ligand not known to be capable of binding to a human AXOR34 polypeptide can bind to such receptor which comprises contacting a yeast or mammalian cell which expresses a human AXOR34 polypeptide with the ligand, such as NmU (e.g., porcine NmU-8 (SEQ ID NO:3), porcine NmU-25 (SEQ ID NO:4), and rat NmU-23 (SEQ ID NO:5)), under conditions permitting binding of candidate ligands to a human AXOR34 polypeptide, and detecting the presence of a candidate ligand which binds to the receptor, thereby determining whether the ligand binds to the human AXOR34 polypeptide. The systems hereinabove described for determining agonists and/or antagonists may also be employed for determining ligands which bind to the receptor.

The present invention also contemplates agonists and antagonists obtainable from the above described screening methods.

Examples of potential human AXOR34 polypeptide antagonists include antibodies or, in some cases, oligonucleotides, which bind to the receptor but do not elicit a second messenger response such that the activity of the receptor is prevented. Potential antagonists also include compounds which are closely related to a ligand of the human AXOR34 polypeptide, i.e. a fragment of the ligand, which has lost biological function and when binding to the human AXOR34 polypeptide, elicits no response.

Thus, in another aspect, the present invention relates to a screening kit for identifying agonists, antagonists, and ligands for AXOR34 polypeptides, which comprises:

(a) a AXOR34 polypeptide, preferably that of SEQ ID NO:2; and further preferably comprises a labeled or unlabeled NmU selected from the group consisting of: porcine NmU-8 (SEQ ID NO:3), porcine NmU-25 (SEQ ID NO:4), and rat NmU-23 (SEQ ID NO:5);

(b) a recombinant cell expressing a AXOR34 polypeptide, preferably that of SEQ ID NO:2; and further preferably comprises a labeled or unlabeled NmU selected from the group consisting of: porcine NmU-8 (SEQ ID NO:3), porcine NmU-25 (SEQ ID NO:4), and rat NmU-23 (SEQ ID NO:5); or (c) a cell membrane expressing AXOR34 polypeptide; preferably that of SEQ ID NO:2; and further preferably comprises a labeled or unlabeled NmU selected from the group consisting of: porcine NmU-8 (SEQ ID NO:3), porcine NmU-25 (SEQ ID NO:4), and rat NmU-23 (SEQ ID NO:5)).

It will be appreciated that in any such kit, (a), (b), or (c) may comprise a substantial component.

Another potential antagonist is a small molecule which binds to the AXOR34 polypeptide receptor, making it inaccessible to ligands such that normal biological activity is prevented. Examples of small molecules include, but are not limited to, small peptides or peptide-like molecules.

Potential antagonists also include soluble forms of AXOR34 polypeptide receptor, e.g., fragments of the receptor, which bind to the ligand and prevent the ligand from interacting with membrane bound AXOR34 polypeptide receptors.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee, et al. *Nucl. Acids Res.,* 6: 3073 (1979); Cooney, et al, *Science,* 241: 456 (1988); and Dervan, et al., *Science,* 251: 1360 (1991)), thereby preventing transcription and production of a KIA0001 receptor polypeptide. The antisense RNA oligonucleotide hybridizes to the mRNA in vivo and blocks translation of the mRNA molecule to AXOR34 polypeptide (antisense—Okano, J., *Neurochem.,* 56: 560 (1991); OLIGODEOXYNUCLEOTIDES AS ANTISENSE INHIBITORS OF GENE EXPRESSION, CRC Press, Boca Raton, Fla. (1988)). The oligonucleotides described above can also be delivered to cells such that the antisense RNA or DNA may be expressed in vivo to inhibit production of a human AXOR34 polypeptide.

Another potential antagonist is a small molecule which binds to a human AXOR34 polypeptide, making it inaccessible to ligands such that normal biological activity is prevented. Examples of small molecules include, but are not limited to, small peptides or peptide-like molecules.

Potential antagonists also include soluble forms of a human AXOR34 polypeptide, e.g., fragments of the polypeptide, which bind to the ligand and prevent the ligand from interacting with membrane bound human AXOR34 polypeptides.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid sidechains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gammacarboxylation, glycosylation, GPI anchor formation, hydroxylation, iodinatiori, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1-12, in Post-translational Covalent Modification of Proteins, B. C. Johnson, Ed., Academic Press, New York, 1983; Seifter et aL, "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occurring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147,195–197, 1981, Advances in Applied Mathematics, 2, 482–489, 1981) and finds the best single region of similarity between two sequences. BEST-FIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448,1988, available as part of the Wisconsin Sequence Analysis Package).

Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies *mutatis mutandis* for other values of the Identity Index, for instance 0.96, 0.97, 0.98 and 0.99.

Similarly, for a polypeptide, a candidate polypeptide sequence having, for example, an dentity Index of 0.95 compared to a reference polypeptide sequence is identical to the eference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:

$n_a$ is the number of nucleotide or amino acid differences, $x_a$ is the total number of nucleotides or amino acids in SEQ ID NO:1 or SEQ ID NO:2, respectively, I is the Identity Index, · is the symbol for the multiplication operator, and in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, often unrelated, fused genes or fragments thereof. In one example, EP-A-0 464 533-A discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLE

Example 1

Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

Example 2

Ligand Bank for Binding and Functional Assays

A bank of over 600 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

Example 3

Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 4

Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 5

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 6

Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is isolated and identified.

Example 7

Calcium and cAMP Functional Assays

7TM receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

Example 8

FLIPR Assay to Identify Ligands of AXOR34

Untransfected HEK-293 cells and HEK-293 cells transiently transfected with AXOR34, or transfected with empty vector (PCDN, were assayed on were assayed on FLIPR (Fluorescent Imaging Plate Reader, Molecular Devices, Sunnyvale, Calif.) for a calcium mobilization response following addition of test ligands. FLIPR for responses to varying concentrations (1 $\mu$M–0.1 nM) of NmU and related ligands. Cells transfected with AXOR34 gave robust calcium mobilization responses to porcine NmU-8 (SEQ ID NO:3), porcine NmU-25 (SEQ ID NO:4), and to rat NmU-23 (SEQ ID NO:5), indicating that AXOR34 is a receptor for NmU. All three of the NmUs that gave robust calcium mobilization responses appeared to be equally potent. There was no concentration-dependent activity for pCDNs or untransfected cells.

What is claimed is:

1. An isolated polynucleotide comprising the polynucleotide sequence set forth in SEQ ID NO:1.

2. An isolated polynucleotide consisting of the polynucleotide sequence set forth in SEQ ID NO:1.

3. An isolated polynucleotide that encodes a polypeptide comprising the amino acid sequence of SEQ ID NO:2.

4. The isolated polynucleotide of claim 1 wherein the polynucleotide encodes the polypeptide of SEQ ID NO:2.

5. A vector comprising the isolated polynucleotide of claim 3.

6. An isolated host cell comprising the vector of claim 5.

7. A process for producing the polypeptide set forth in SEQ ID NO:2, said method comprising the step of culturing a host cell of claim 6 under conditions sufficient for the production of said polypeptide.

8. A membrane of a recombinant host cell of claim 6 expressing said polypeptide.

* * * * *

SEQUENCE LISTING

<160> NUMBER OF SEQ ID NOS: 5

<210> SEQ ID NO 1
<211> LENGTH: 1248
<212> TYPE: DNA
<213> ORGANISM: HOMO SAPIENS

<400> SEQUENCE: 1

```
atgtcaggga tggaaaaact tcagaatgct tcctggatct accagcagaa actagaagat      60
ccattccaga aacacctgaa cagcaccgag gagtatctgg ccttcctctg cggacctcgg     120
cgcagccact tcttcctccc cgtgtctgtg gtgtatgtgc caattttttgt ggtgggggtc    180 attggcaatg tcctggtgtg cctggtgatt ctgcagcacc aggctatgaa gacgcccacc    240
aactactacc tcttcagcct ggcggtctct gacctcctgg tcctgctcct tggaatgccc    300
ctggaggtct atgagatgtg gcgcaactac cctttcttgt tcgggcccgt gggctgctac    360
ttcaagacgg ccctctttga gaccgtgtgc ttcgcctcca tcctcagcat caccaccgtc    420
agcgtggagc gctacgtggc catcctacac ccgttccgcg ccaaactgca gagcacccgg    480
cgccgggccc tcaggatcct cggcatcgtc tggggcttct ccgtgctctt ctccctgccc    540
aacaccagca tccatggcat caagttccac tacttcccca atgggtccct ggtcccaggt    600
tcggccacct gtacggtcat caagcccatg tggatctaca atttcatcat ccaggtcacc    660
tccttcctat tctacctcct ccccatgact gtcatcagtg tcctctacta cctcatggca    720
ctcagactaa agaaagacaa atctcttgag gcagatgaag ggaatgcaaa tattcaaaga    780
```

-continued

```
ccctgcagaa aatcagtcaa caagatgctg tttgtcttgg tcttagtgtt tgctatctgt    840
tgggccccgt tccacattga ccgactcttc ttcagctttg tggaggagtg gactgaatcc    900
ctggctgctg tgttcaacct cgtccatgtg gtgtcaggtg tcttattcta cctgagctca    960
gctgtcaacc ccattatcta taacctactg tctcgccgct tccaggcagc attccagaat   1020
gtgatctctt ctttccacaa acagtggcac tcccagcatg acccacagtt gccacctgcc   1080
cagcggaaca tcttcctgac agaatgccac tttgtggagc tgaccgaaga tataggtccc   1140
caattcctat gtcagtcatc cgtgcacaac tctcacctcc aacagccct ctctagtgaa    1200 cagatgtcaa gaacaaacta tcaaagcttc cactttaaca aaacctga               1248
```

<210> SEQ ID NO 2
<211> LENGTH: 415
<212> TYPE: PRT
<213> ORGANISM: HOMO SAPIENS

<400> SEQUENCE: 2

```
Met Ser Gly Met Glu Lys Leu Gln Asn Ala Ser Trp Ile Tyr Gln Gln
  1               5                  10                  15

Lys Leu Glu Asp Pro Phe Gln Lys His Leu Asn Ser Thr Glu Glu Tyr
             20                  25                  30

Leu Ala Phe Leu Cys Gly Pro Arg Arg Ser His Phe Phe Leu Pro Val
         35                  40                  45

Ser Val Tyr Val Pro Ile Phe Val Val Gly Val Ile Gly Asn Val
     50                  55                  60

Leu Val Cys Leu Val Ile Leu Gln His Gln Ala Met Lys Thr Pro Thr
 65                  70                  75                  80

Asn Tyr Tyr Leu Phe Ser Leu Ala Val Ser Asp Leu Leu Val Leu Leu
                 85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
            180                 185                 190

Pro Asn Gly Ser Leu Val Pro Gly Ser Ala Thr Cys Thr Val Ile Lys
        195                 200                 205

Pro Met Trp Ile Tyr Asn Phe Ile Ile Gln Val Thr Ser Phe Leu Phe
    210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Phe Val
            260                 265                 270

Leu Val Leu Val Phe Ala Ile Cys Trp Ala Pro Phe His Ile Asp Arg
        275                 280                 285

Leu Phe Phe Ser Phe Val Glu Glu Trp Thr Glu Ser Leu Ala Ala Val
```

-continued

```
                 290                 295                 300
Phe Asn Leu Val His Val Val Ser Gly Val Leu Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
                340                 345                 350

His Asp Pro Gln Leu Pro Pro Ala Gln Arg Asn Ile Phe Leu Thr Glu
                355                 360                 365

Cys His Phe Val Glu Leu Thr Glu Asp Ile Gly Pro Gln Phe Leu Cys
                370                 375                 380

Gln Ser Ser Val His Asn Ser His Leu Pro Thr Ala Leu Ser Ser Glu
385                 390                 395                 400

Gln Met Ser Arg Thr Asn Tyr Gln Ser Phe His Phe Asn Lys Thr
                    405                 410                 415

<210> SEQ ID NO 3
<211> LENGTH: 8
<212> TYPE: PRT
<213> ORGANISM: HOMO SAPIENS

<400> SEQUENCE: 3

Tyr Phe Leu Phe Arg Pro Arg Asn
1               5

<210> SEQ ID NO 4
<211> LENGTH: 25
<212> TYPE: PRT
<213> ORGANISM: HOMO SAPIENS

<400> SEQUENCE: 4

Phe Leu Val Asp Glu Glu Phe Gln Gly Pro Ile Val Ser Gln Asn Arg
1               5                   10                  15

Arg Tyr Phe Leu Phe Arg Pro Arg Asn
                20                  25

<210> SEQ ID NO 5
<211> LENGTH: 23
<212> TYPE: PRT
<213> ORGANISM: HOMO SAPIENS

<400> SEQUENCE: 5

Tyr Lys Val Asn Glu Tyr Gln Gly Pro Val Ala Pro Ser Gly Gly Phe
1               5                   10                  15

Phe Leu Phe Arg Pro Arg Asn
                20
```